(12) United States Patent
Domb

(10) Patent No.: US 7,026,290 B1
(45) Date of Patent: Apr. 11, 2006

(54) DISPERSIBLE CONCENTRATE FOR THE DELIVERY OF CYCLOSPRIN

(75) Inventor: Abraham J. Domb, Efrat (IL)

(73) Assignee: Dexcel Ltd., Hadera (IL)

( * ) Notice: Subject to any disclaimer, the term of this patent is extended or adjusted under 35 U.S.C. 154(b) by 0 days.

(21) Appl. No.: 09/869,519

(22) PCT Filed: Dec. 30, 1999

(86) PCT No.: PCT/IL99/00710

§ 371 (c)(1),
(2), (4) Date: Sep. 17, 2001

(87) PCT Pub. No.: WO00/40219

PCT Pub. Date: Jul. 13, 2000

Related U.S. Application Data

(63) Continuation-in-part of application No. 09/223,378, filed on Dec. 30, 1998, now abandoned.

(51) Int. Cl.
*A61K 38/13* (2006.01)

(52) U.S. Cl. .............................. 514/11; 514/9

(58) Field of Classification Search .............. 514/9, 514/11
See application file for complete search history.

(56) References Cited

U.S. PATENT DOCUMENTS

| | | |
|---|---|---|
| 4,117,118 A | 9/1978 | Härri et al. |
| 4,215,199 A | 7/1980 | Härri et al. |
| 4,388,307 A | 6/1983 | Cavanak |
| 5,154,930 A | 10/1992 | Popescu et al. |
| 5,156,960 A | 10/1992 | Jekkel née Bokány et al. |
| 5,188,837 A | 2/1993 | Domb |
| 5,227,165 A | 7/1993 | Domb et al. |
| 5,272,068 A | 12/1993 | Ruby et al. |
| 5,340,588 A | 8/1994 | Domb |
| 5,342,625 A | 8/1994 | Hauer et al. |
| 5,378,475 A | 1/1995 | Smith et al. |
| 5,382,655 A | 1/1995 | Szánya et al. |
| 5,409,816 A | 4/1995 | Lundell et al. |
| 5,430,017 A | 7/1995 | Antalné et al. |
| 5,430,021 A | 7/1995 | Rydnic et al. |
| 5,447,854 A | 9/1995 | Goto et al. |
| 5,472,706 A | 12/1995 | Friedman et al. |
| 5,529,785 A | 6/1996 | Dietl |
| 5,543,393 A | 8/1996 | Kim et al. |
| 5,573,783 A | 11/1996 | Desieno et al. |
| 5,576,016 A | 11/1996 | Amselem et al. |
| 5,583,105 A | 12/1996 | Kovacs et al. |
| 5,589,455 A | 12/1996 | Woo |
| 5,603,951 A | 2/1997 | Woo |
| 5,614,491 A | 3/1997 | Walch et al. |
| 5,616,595 A | 4/1997 | Chu et al. |
| 5,637,317 A | 6/1997 | Dietl |

(Continued)

FOREIGN PATENT DOCUMENTS

| | | |
|---|---|---|
| CH | 679118 A5 | 9/1989 |
| DE | 3930928 C2 | 9/1989 |
| EP | 0034567 B1 | 2/1981 |
| EP | 0243446 B1 | 10/1986 |
| EP | 0287036 B1 | 4/1988 |
| EP | 0296122 B1 | 6/1988 |
| EP | 0418248 B1 | 2/1989 |
| EP | 0633029 B1 | 4/1989 |
| EP | 0444081 B1 | 11/1989 |
| EP | 0379708 B1 | 12/1989 |
| EP | 0379045 B1 | 1/1990 |
| EP | 0388152 B1 | 3/1990 |
| EP | 0474647 B1 | 3/1990 |
| EP | 0391369 B1 | 4/1990 |
| EP | 0502119 B1 | 11/1990 |
| EP | 0521074 B1 | 3/1991 |
| EP | 0507968 B1 | 4/1991 |
| EP | 0512109 B1 | 11/1991 |
| EP | 0724429 B1 | 2/1992 |
| EP | 0580817 B1 | 4/1992 |
| EP | 0539319 B1 | 6/1992 |
| EP | 0572942 B1 | 5/1993 |
| EP | 0589843 A1 | 9/1993 |
| EP | 0598337 B1 | 11/1993 |
| EP | 0677116 B1 | 12/1993 |
| EP | 0635261 B1 | 7/1994 |
| EP | 0697214 A1 | 7/1994 |
| EP | 0649651 A1 | 9/1994 |
| EP | 0724452 B1 | 9/1994 |
| EP | 0726760 B1 | 10/1994 |
| EP | 0651995 B1 | 11/1994 |
| EP | 0740547 B1 | 1/1995 |
| EP | 0725076 A1 | 2/1995 |
| EP | 0756489 B1 | 5/1995 |
| EP | 0769938 B1 | 6/1995 |
| EP | 0801686 B1 | 7/1995 |
| EP | 0760237 A1 | 8/1995 |
| EP | 0799013 B1 | 12/1995 |
| EP | 0793966 A1 | 3/1997 |
| FR | 2636534 A1 | 9/1989 |
| GB | 2 278 780 | 5/1994 |
| IE | 60764 | 9/1989 |
| SE | 514303 | 9/0000 |

(Continued)

*Primary Examiner*—Robert A. Wax

(57) ABSTRACT

A formulation for the administration of a cyclosporin. This formulation features a hydrophilic solvent which is characterized by being a lower alkyl ester of hydroxyalkanoic acid; and a surfactant, preferably a combination of a surfactant with a high HLB (hydrophilic/lipophilic balance) of at least about 8 and a surfactant with a low HLB of less than about 5. Other ingredients are optional, such as a fatty acid ester such as tricaprin, a phospholipid, and an ethoxylated fat such as Cremophor or another similar substance. Optionally, the ethoxylated fat is substituted for the surfactant. The preferred particle size of the resultant formulation is less than about 100 nm, more preferably less than about 60 nm, and most preferably from about 5 nm to about 50 nm. The formulation of the present invention is characterized by having high bioavailability.

49 Claims, 3 Drawing Sheets

U.S. PATENT DOCUMENTS

| | | |
|---|---|---|
| 5,639,474 A | 6/1997 | Woo |
| 5,639,724 A | 6/1997 | Cavanak |
| 5,641,745 A | 6/1997 | Ramtoola |
| 5,645,856 A | 7/1997 | Lacy et al. |
| 5,650,170 A | 7/1997 | Wright et al. |
| 5,651,980 A | 7/1997 | Lanza et al. |
| 5,656,287 A | 8/1997 | Adler-Moore et al. |
| 5,656,459 A | 8/1997 | Balaraman et al. |
| 5,660,856 A | 8/1997 | Adler-Moore et al. |
| 5,660,858 A | 8/1997 | Parikh et al. |
| 5,662,932 A | 9/1997 | Amselem et al. |
| 5,665,386 A | 9/1997 | Benet et al. |
| 5,670,166 A | 9/1997 | Adler-Moore et al. |
| 5,670,478 A | 9/1997 | Stuchlik et al. |
| 5,683,714 A | 11/1997 | Adler-Moore et al. |
| 5,688,525 A | 11/1997 | Adler-Moore et al. |
| 5,709,797 A | 1/1998 | Bocchiola et al. |
| 5,716,928 A | 2/1998 | Benet et al. |
| 5,739,105 A | 4/1998 | Kim et al. |
| 5,741,512 A | 4/1998 | Hauer et al. |
| 5,747,330 A | 5/1998 | Casareto et al. |
| 5,750,142 A | 5/1998 | Friedman et al. |
| 5,756,450 A | 5/1998 | Hahn et al. |
| 5,759,566 A | 6/1998 | Poli et al. |
| 5,759,997 A | 6/1998 | Cavanak |
| 5,798,333 A | 8/1998 | Sherman |
| 5,801,020 A | 9/1998 | Casareto et al. |
| 5,827,822 A | 10/1998 | Floc'h et al. |
| 5,830,505 A | 11/1998 | Fischer et al. |
| 5,856,141 A | 1/1999 | Kim et al. |
| 5,858,410 A | 1/1999 | Muller et al. |
| 5,866,159 A | 2/1999 | Hauer et al. |
| 5,874,572 A | 2/1999 | Kim et al. |
| 5,891,845 A | 4/1999 | Myers |
| 5,891,846 A | 4/1999 | Ishida et al. |
| 5,912,005 A | 6/1999 | Lanza et al. |
| 5,916,589 A | 6/1999 | Hauer et al. |
| 5,929,030 A | 7/1999 | Hamied et al. |
| 5,932,243 A | 8/1999 | Fricker et al. |
| 5,958,378 A | 9/1999 | Waldrep et al. |
| 5,958,458 A | 9/1999 | Norling et al. |
| 5,958,876 A | 9/1999 | Woo |
| 5,962,014 A | 10/1999 | Hauer et al. |
| 5,962,017 A | 10/1999 | Hauer et al. |
| 5,962,019 A | 10/1999 | Cho et al. |
| 5,965,160 A | 10/1999 | Benita et al. |
| 5,968,972 A | 10/1999 | Broder et al. |
| 5,976,381 A | 11/1999 | Lundell et al. |
| 5,977,066 A | 11/1999 | Cavanak |
| 5,980,939 A | 11/1999 | Kim et al. |
| 5,985,321 A | 11/1999 | Brox et al. |
| 5,989,583 A | 11/1999 | Amselem |
| 5,998,365 A | 12/1999 | Sherman |
| 6,008,192 A | 12/1999 | Al-Razzak et al. |
| 6,028,067 A | 2/2000 | Hong et al. |
| 6,057,289 A | 5/2000 | Mulye |
| 6,255,100 B1 | 7/2001 | Ko et al. |
| 6,267,985 B1 | 7/2001 | Chen et al. |
| 6,306,306 B1 | 10/2001 | Voigt et al. |
| 2001/0025025 A1 | 9/2001 | Viskov |
| 2003/0022944 A1 * | 1/2003 | Gumkowski et al. |

FOREIGN PATENT DOCUMENTS

| | | |
|---|---|---|
| WO | WO 93/15736 | 8/1993 |
| WO | WO95/01785 | 1/1995 |
| WO | WO 95/01786 | 1/1995 |
| WO | WO96/12031 | 4/1996 |
| WO | WO96/12032 | 4/1996 |
| WO | WO96/13273 | 5/1996 |
| WO | WO 96/14079 | 5/1996 |
| WO | WO 96/27607 | 9/1996 |
| WO | WO 96/36316 | 11/1996 |
| WO | WO 97/07787 | 3/1997 |
| WO | WO 97/10849 | 3/1997 |
| WO | WO97/19692 | 6/1997 |
| WO | WO 97/20548 | 6/1997 |
| WO | WO97/22358 | 6/1997 |
| WO | WO97/26003 | 7/1997 |
| WO | WO97/34918 | 9/1997 |
| WO | WO97/36610 | 10/1997 |
| WO | WO 97/44053 | 11/1997 |
| WO | WO97/46575 | 12/1997 |
| WO | WO97/46580 | 12/1997 |
| WO | WO97/48410 | 12/1997 |
| WO | WO98/30204 | 7/1998 |
| WO | WO 98/30205 | 7/1998 |
| WO | WO98/33512 | 8/1998 |
| WO | WO98/40051 | 9/1998 |
| WO | WO98/42734 | 10/1998 |
| WO | WO 98/58629 | 12/1998 |
| WO | WO99/00002 | 1/1999 |
| WO | WO99/56727 | 11/1999 |
| WO | WO00/03753 | 1/2000 |
| WO | WO00/06120 | 2/2000 |
| WO | WO00/18374 | 4/2000 |
| WO | WO00/30615 | 6/2000 |
| WO | WO00/40219 | 7/2000 |
| WO | WO00/72867 | 12/2000 |

* cited by examiner

DISPERSIBLE CONCENTRATE FOR THE DELIVERY OF CYCLOSPRIN

This application is a national stage entry under 35 USC 371 of PCT/IL99/00710, filed Dec. 30, 1999, which is a continuation-in-part of Ser. No. 09/223,378, filed Dec. 30, 1998, now abandoned.

FIELD AND BACKGROUND OF THE INVENTION

The present invention is of a dispersible concentrate preparation for the delivery of cyclosporin, and in particular, of a dispersible concentrate preparation which provides a delivery system with high bioavailability of cyclosporin and related substances.

Many dispersion systems are currently in use as, or being explored for use as, carriers of substances, particularly biologically active compounds. These systems are designed to protect the substance from the environment during delivery and to provide a controlled release of the substance to a targeted area. In some cases, the goal is to target specific sites in the body using the dispersion. In other cases, the goal is to prepare a drug carrier system that acts as a reservoir at the site of injection.

Dispersion systems used for pharmaceutical and cosmetic formulations can be categorized as either suspensions or emulsions. Suspensions are defined as solid particles ranging in size from a few nanometers up to hundreds of microns, dispersed in an aqueous or nonaqueous medium using suspending agents. Solid particles include microspheres, microcapsules, and nanospheres.

Emulsions can be defined as dispersions of one liquid in another, stabilized by an interfacial film of emulsifiers such as surfactants and lipids. Despite their long history, emulsions are used less often today than many other dosage forms due to the inherent instability. Emulsion formulations include water in oil and oil in water emulsions, multiple water/oil/water emulsions, microemulsions, microdroplets, and liposomes.

A microemulsion is a transparent or substantially transparent emulsion which is formed spontaneously or substantially spontaneously when its components are brought into contact. Microemulsions are thermodynamically stable and contain dispersed particles or droplets of a size less than about 200 nm. Generally microemulsions feature droplets or particles having a mean diameter of less than about 150 nm. These particles may be spherical, although other structures are feasible, such as liquid crystals with lamellar, hexagonal or isotropic symmetries. Microemulsions are usually stable over periods in excess of 24 hours.

Microemulsions can also be used as a "microemulsion preconcentrate", defined herein as a composition which spontaneously forms a microemulsion in an aqueous medium, for example in water, upon dilution, or in the gastric juices after oral application. Dilution of the microemulsion in water can be for example from about 1:1 fold to about 1:10 fold dilution.

As noted above, while emulsion based delivery systems are useful for certain applications, the delivering vesicles are subject to physical rupture because of the delicate nature of the liquid/membrane/liquid structure. Emulsion based delivery systems also have relatively short release times. Further, it is difficult to isolate emulsion based vesicles from the aqueous media used for storage for subsequent reconstitution.

In spite of these difficulties, microemulsions have been the only successful delivery systems for certain types of pharmaceutical compounds, particularly compounds such as members of the cyclosporin class, which are cyclic oligopeptides. The cyclosporin class includes substances having pharmaceutical utility, for example as immunosuppressive agents, anti-parasitic agents and agents for the reversal of multi-drug resistance, as known and described in the art. Examples of such cyclosporins include, but are not limited to, Cyclosporin A (also known as and referred to herein as "Ciclosporin"), Cyclosporin G, [0-(2-hydroxyethyl)-(D)Ser]$^2$-Ciclosporin and [3'-deshydroxy-3'-ket-MeBmt]$^1$-[Val)]$^2$-Ciclosporin.

The first of the cyclosporins to be isolated was the naturally occurring fungal metabolite Ciclosporin (Cyclosporine). Ciclosporin is the cyclosporin of formula (I):

```
┌MeBmt-eAbu-Ser-MeLeu-Val-MeLeu-Ala-(D)Ala-MeLeu-MeLeu-MeVal┐
│  1     2   3    4    5    6    7     8      9     10    11  │
└─────────────────────────────────────────────────────────────┘
``` wherein —MeBmt— represents the N-methyl-(4R)-4-but-2E-en-1-yl-4-methyl-(L)threonyl residue of formula (II):

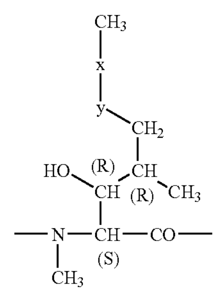

in which —x-y— is —CH═CH— (trans). Ciclosporin is well known as an immunosupressive agent. In addition, Ciclosporin is being examined for the treatment of autoimmune and inflammatory diseases.

Since the original discovery of Ciclosporin, a wide variety of naturally occurring cyclosporins have been isolated and identified, and many further non-natural cyclosporins have been prepared by total- or semi-synthetic means or by the application of modified culture techniques. The class comprised by the cyclosporins now includes, for example, the naturally occurring cyclosporins A through Z [c.f. Traber et al., *Helv. Chim. Acta.* 60: 1247–1255, 1977; Traber et al.. *Helv. Chim. Acta.* 65: 1655–1667, 1982; Kobel el al., *Europ. J. App. Microbio. and Biotech.,* 14: 273–240 (1982); and von Wartburg el al., *Progress in Allergy,* 38: 28–45 (1986)], as well as various non-natural cyclosporin derivatives and artificial or synthetic cyclosporins including: the so-called dihydro-cyclosporins, in which the moiety —x-y— of the —MeBmt— residue in Formula (II) above is saturated to give —x-y— of —$CH_2$—$CH_2$—; derivatized cyclosporins (e.g. in which a further substituent is introduced at the α-carbon atom of the sarcosyl residue at the 3-position of the cyclosporin molecule); cyclosporins in which the —MeBmt— residue is present in isomeric form (e.g. in which the configuration across positions 6' and 7' of the —MeBmt— residue is cis rather than trans); and cyclosporins in which variant amino acids are incorporated at specific positions within the peptide sequence. Many of these members of the cyclosporin class exhibit pharmaceutical utility which may be comparable to that of Ciclosporin.

Unfortunately, many difficulties have been encountered in the effective administration of Ciclosporin, difficulties which appear to be inherent in the nature of the members of the cyclosporin class. Cyclosporins are characteristically highly hydrophobic, and thus require a lipophilic carrier. The selection of a suitable carrier is particularly critical for the administration of cyclosporins, as the bioavailability of these compounds is known in the art to be highly variable, depending upon the properties of the carrier. Furthermore, these compounds are known to have bioavailability which may vary significantly between individuals. Such variation is particularly dangerous given the side effects of cyclosporins, such as nephrotoxicity. Thus, the suitable carrier must provide good bioavailability of cyclosporins which is substantially consistent between individuals.

As noted previously, cyclosporins may be administered with a microemulsion carrier. This carrier generally contains a hydrophilic solvent, such as liquid PEG200-600, ethylene or propylene glycol, ethanol or propanol, glycerin, water soluble fatty acid C6–C18 esters of sucrose, dimethylisosorbide, ethyl-acetate, glycofurol (fatty acid derivative of a cyclic polyol), PEG derivatives of tocopherol, or PEG-fatty acid esters; a surfactant, such as Tween 20, various PEG (polyethylene glycol) derivatives or phospholipids; a water insoluble oil such as corn oil and other oils from plants and mixtures of oils; and Cremophor™ and similar PEG derivatives of castor oil or other fats which are used as an amphiphilic solvent, emulsifier, surfactant and so forth. Unfortunately, none of these background art formulations provides high bioavailability for cyclosporin.

The currently commercially available formulation is disclosed in U.S. Pat. No. 5,342,625 to Sandoz A.G. This formulation includes a hydrophilic phase, a lipophilic phase and a surfactant. The hydrophilic phase could be a $C_{1-5}$ alkyl di-or partial-ether of a mono- or poly-oxy-$C_{1-12}$alkanediol, for example.

PCT Application No. WO 96/13273 to Sandoz describes compositions for cyclosporin and other macrolide drugs such as Rapamycin, containing a hydrophilic phase which includes dimethylisosorbide and/or a lower alkyl alkanoic ester, a lipophilic phase and a surfactant. The particle size after dispersion can be 200 nm but is preferably 100 nm or less. The hydrophilic phase is PEG, propylene glycol and glycofurol or dimethylisosorbide (a bicyclic ether). The bioavailability of a composition containing cyclosporin and the carrier is not disclosed.

PCT Application No. WO 97/19692, also to Sandoz, describes compositions which are based on PEG-derivatives of saturated hydroxy fatty acids such as PEG-hydroxystearate and a low alcohol such as ethanol or propylene glycol. Again, the bioavailability of such a composition is not disclosed.

PCT Application No. WO 98/33512 to Novartis describes compositions for oral administration of cyclosporin which do not contain oil. Instead, these compositions contain a surfactant with HLB 10 or higher and a hydrophilic phase which is polyethylene glycol and/or a lower alcohol (not more than 12%). The formulations are preconcentrates which provide a particle size of 10 to 150 nm upon dispersion. The disclosed advantage of these compositions is their ability to be stably contained within a hard capsule. However, no specific data is disclosed related to the bioavailability of cyclosporin with this composition. As noted above, the bioavailability of cyclosporin is known to be highly variable, depending upon the carrier.

PCT Application No. WO 97/04795 to POLI Industria describes compositions that must contain one polymer, linear or crosslinked PEG and poly (acrylic) or mixtures thereof and monoesters of fatty acids with a short alcohol. Again, the bioavailability of such a composition is not disclosed.

U.S. Pat. No. 5,756,450 to Novartis describes solid formulations for cyclosporin composed of a water soluble monoester of a fatty acid C6–C18 with a polyol, for example a saccharide such as Saccharose monolaurate or raffinose monolaurate. This solvent can be used in combination with other water soluble solvents including PEG, ethanol, ethylene glycol and glycerin. The examples describe solid solutions (powder) of Cyclosporin in saccharose monooleate which is completely soluble in water. Again, the bioavailability of such a composition is not disclosed.

U.S. Pat. Nos. 5,603,951 and 5,639,474 to Hanmi Pham. describe compositions of dimethylisosorbide as a cosurfactant and a primary alcohol, medium chain triglycerides and a surfactant having a HLB value of 10 to 17 such as Tween 20, formulated in soft gelatin capsule. The particle size is about 100 nm. Again, the bioavailability of such a composition is not disclosed.

U.S. Pat. No. 5,583,105 to Biogel describes cyclosporin formulations composed of PEG esters of tocopherol and a lipophilic solvent, an amphiphilic solvent and ethanol. Again, the bioavailability of such a composition is not disclosed.

U.S. Pat. No. 5,614,491 to Dr. Rentschler GmbH, describes formulations of PEG fatty acid monoesters as emulsifying agent and a polyol as solvent. U.S. Pat. No. 5,798,333 to Sherman describes formulations composed of Tochersolan and a polyhydric alcohol. Tochersolan is a water soluble surfactant which dissolves cyclosporin only at a 7:1 ratio.

U.S. Pat. No. 5,827,822 to Sangstat describes formulations of alcohol and a PEG surfactant forming particle size between 200 and 400 nm.

European Patent Application No. EP 0760237 A1 to Cipla describes a composition containing: vegetable oil triglycerides (castor, peanut, or coconut oil), phospholipid, a surfactant (Tween 20, polyoxyl-40-hydrogenated castor oil), and a hydrophilic solvent, propylene glycol. Again, the bioavailability of cyclosporin administered with such a composition is not disclosed.

None of these disclosed background art carrier formulations features a hydrophilic solvent which is a lower alkyl ester of hydroxyalkanoic acid, such as ethyl lactate or N-methyl pyrrolidone. Moreover, none of these disclosed background art carrier formulations features a combination of a surfactant with high HLB and a surfactant with low HLB. Furthermore, none of these background art carrier formulations is disclosed as having high bioavailability. Thus, the background art carrier formulations do not appear to possess the advantageous high bioavailability of the present invention, as described in greater detail below.

There is thus an unmet need for, and it would be useful to have, a composition for the administration of cyclosporins, particularly for oral administration, which would provide a high bioavailability, and which would preferably contain a hydrophilic solvent which is a lower alkyl ester of hydroxyalkanoic acid, and a surfactant which is preferably a combination of a surfactant with high HLB and a surfactant with low HLB.

SUMMARY OF THE INVENTION

The present invention is of a novel formulation for the administration of a cyclosporin. This formulation features a hydrophilic solvent which is characterized by being a lower alkyl ester of hydroxyalkanoic acid; and a surfactant, preferably a combination of a surfactant with a high HLB (hydrophilic/lipophilic balance) of at least about 8 and a surfactant with a low HLB of less than about 5.

Other ingredients are optional, such as a fatty acid ester such as tricaprin, a phospholipid, and an ethoxylated fat such as Cremophor™ or another similar substance.

The preferred mean diameter of the particle of the resultant formulation is less than about 100 nm, more preferably less than about 60 nm, and most preferably from about 5 nm to about 50 nm.

Hereinafter, the term "dispersible concentrate" includes those compositions featuring droplets or particles having a mean diameter of less than about 150 nm. Hereinafter, the term "nanodispersion preconcentrate" refers to a composition which spontaneously forms a nanodispersion in an aqueous medium, for example in water upon dilution, or in the gastric juices after oral application. Dilution of the nanodispersion preconcentrate in water can be for example from about 1:1 fold to about 1:10 fold dilution.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
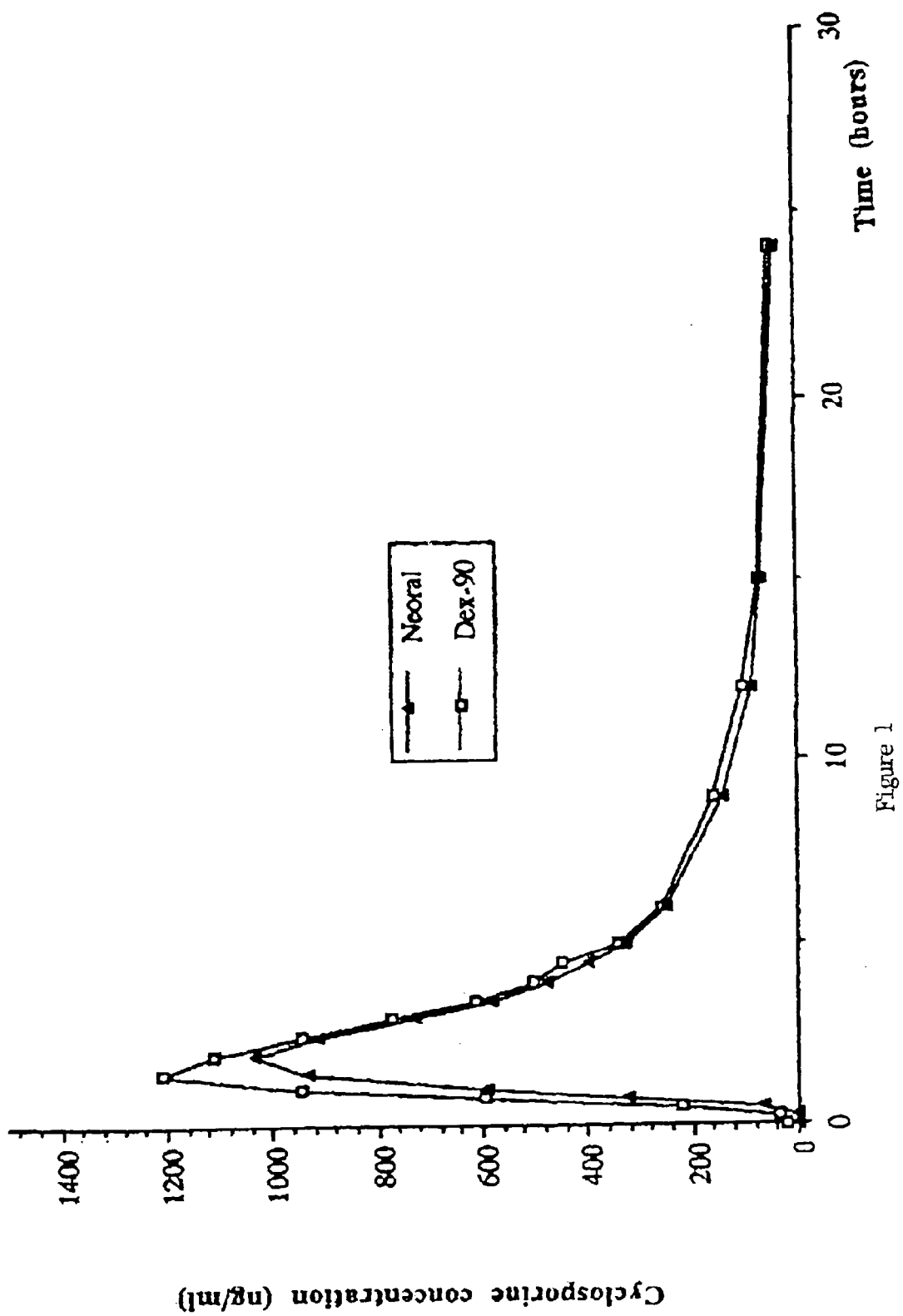
FIG. 1 is a graph of cyclosporin blood concentration after oral administration of 4 capsules of 50 mg cyclosporin in a first dispersible concentrate formulation of the invention.

The present invention is of a novel formulation for the administration of a cyclosporin. This formulation features a hydrophilic solvent which is characterized by being a lower alkyl ester of hydroxyalkanoic acid; and a surfactant, preferably a combination of a surfactant with a high HLB (hydrophilic/lipophilic balance) of at least about 8 and a surfactant with a low HLB of less than about 5. The hydrophilic solvent is preferably ethyl lactate.

Other ingredients are optional, such as a fatty acid ester such as tricaprin, a phospholipid, and an ethoxylated fat such as Cremophor™ or another similar substance. Optionally, a sufficient amount of the ethoxylated fat such as Cremophor™ is substituted for the surfactant.

Another advantage of the present invention is that solid fats, such as tricaprin, are suitable for use with the formulations of the present invention and may optionally be incorporated therein. Hereinafter, the terms "solid fat" and "liquid fat" refer to fats which are solid or liquid, respectively, at room temperature.

Preferably, the composition of the present invention does not include an alcohol such as ethanol.

The preferred particle size of the resultant formulation is less than about 100 nm, more preferably less than about 60 nm, and most preferably from about 5 nm to about 50 nm. In fact, as described in greater detail below, the resultant formulation must have a particle size of less than about 100 nm in order to be suitable for the administration of cyclosporin.

As described in greater detail below, the combination of these components has unexpectedly been shown to provide higher bioavailability than had been previously shown for formulations of cyclosporin. Furthermore, the formulations of the present invention have the advantage of not requiring stabilizers, such as anti-oxidants, in order to obtain good stability characteristics. Without wishing to be limited to a single mechanism, it is hypothesized that the excellent stability of the formulations of the present invention is due to the use of hydrophilic solvents such as ethyl lactate.

Ethyl lactate, and other members of this family of solvents, have unexpectedly good properties for such a formulation as the formulations of the present invention. For example, ethyl lactate is miscible in both organic and inorganic solvents, since it is more hydrophobic than ethanol. Ethyl lactate has higher storage stability than ethanol. Ethanol is a highly volatile solvent, with correspondingly lower storage stability, such that the use of ethanol in the currently available background art formulations is a clear disadvantage of these formulations. Furthermore, these background art formulations require a combination of ethanol and propylene glycol in order to stabilize the alcohol, which is another disadvantage of incorporating ethanol into a formulation, a disadvantage which is overcome by the formulations of the present invention.

The present invention may be more readily understood with reference to the following illustrative examples. It should be noted that reference is made generally to "cyclosporin", indicating any member of the cyclosporin class having pharmaceutical efficacy. The particularly preferred member of the cyclosporin class is Ciclosporin (Cyclosporin A). The preparation of the microemulsion compositions of the present invention is described first with reference to the following general description and then with reference to the following non-limiting examples of the preparation and application of the compositions of the present invention.

Hydrophilic Solvent

First, as noted previously, a suitable hydrophilic organic solvent must be selected. The solvent is preferably selected from the family of lower alkyl esters of hydroxyalkanoic acid or from the family of lower alkyl esters of N-alkyl pyrrolidone. Hereinafter, the term "lower alkyl" includes $C_1$ to $C_4$, for example ethyl. The preferred hydrophilic solvents of the present invention are C1-4 alkyl-hydroxy alkanoic acid ester, or N-C1–4 alkyl pyrrolidone. More preferably, the hydrophilic solvent is selected from the group consisting of ethyl lactate or N-methyl pyrrolidone.

Ethyl lactate (2-hydroxypropanoic acid ethyl ester), is a colorless liquid which is miscible with water, alcohol and ether. Ethyl lactate is considered to be suitable for human administration, with an $LD_{50}$ which was higher than 5 g/kg in mice when given an oral dose. N-methyl pyrrolidone is a colorless liquid which is miscible with water and organic solvents, and is also considered to be safe for human administration. N-methyl pyrrolidone is used in the clinic as a solvent for a polymeric in situ implant to treat gingivitis.

Alternatively and more preferably, a combination of a solvent selected from the family of lower alkyl esters of hydroxyalkanoic acid and a solvent selected from the family of lower alkyl esters of N-alkyl pyrrolidone is employed. Optionally, any of these solvents can be combined with other hydrophilic organic solvents such as ethylene glycol, glycofurol or PEG 400. These hydrophilic solvents have not been previously taught or suggested as being suitable for cyclosporins.

Surfactant

Second, a suitable surfactant is preferably selected, although optionally, a sufficient amount of an ethoxylated fat such as Cremophor™ is substituted for the surfactant, as described in greater detail below.

If a surfactant is used, the surfactant is preferably a combination of a surfactant with a high HLB (hydrophilic/lipophilic balance) of at least about 8 and a surfactant with a low HLB of less than about 5. The term "HLB" refers to the hydrophilic/lipophilic balance of a surfactant. A surfactant with high HLB is hydrophilic, while a surfactant with low HLB is hydrophobic. Therefore, the combination of a surfactant with high HLB and a surfactant with low HLB, as is preferred for the compositions of the present invention, is actually a combination of a hydrophilic surfactant and a hydrophobic surfactant. This combination has never been taught or suggested in the background art as being suitable for a pharmaceutical carrier for cyclosporins. Where the HLB of the surfactant has been specified in the background art, it has been given in the range of 8 to 20, which is clearly different from the combination of surfactants taught herein. Thus, the compositions of the present invention can be clearly differentiated from those taught in the background art on the basis of the preferred combination of a surfactant with a low HLB and a surfactant with a high HLB.

Particularly preferred combinations of these surfactants feature a large difference between the HLB of the low HLB surfactant and that of the high HLB surfactant. Therefore, one example of such a particularly preferred combination is a combination of Tween™ 20 and Span™ 80, although of course other such combinations could be also be used.

Span™ hydrophobic surfactants are a group of sorbitan fatty acid esters such as sorbitan monooleate. sorbitan monopalmitate. sorbitan monostearate, sorbitan tristearate, sorbitan monooleate, sorbitan trioleate and sorbitan monolaurate (Fiedler, H. P., "Lexikon der Hilfsstoffe fur Pharmazie, Kosmetic und Angrenzende Gebiete", Editio Cantor, D-7960 Aulendorf, 3rd edition, 1989, pages 1139–1140). Span™ 80 is an example of a low HLB surfactant, with an HLB of 4.3, and is sorbitan monooleate. They are commercially available from various producers, which include but are not limited to, Capital City Products, Croda Chem, ICI, Lippo Chem. and Atlas, under various commercial names: Arlacel™, Armotan™, Crill™, Emsorb™, Liposorb™, Protachem™, and Sorbester™.

Examples of suitable surfactants from this group, with HLB values given in parentheses, are as follows: Span™ 60 (4.7), Span™ 65 (2.1), Span™ 80 (4.3), Span™ 85 (1.8), Arlacel™ 83 (3.7), Arlacel™ C (3.7), Arlacel™ 85 (1.8), Arlacel™ 80 (4.3), and Arlacel™ 60 (4.7). These molecules are generally soluble in oil. They are also soluble in most organic solvents. In water they are generally insoluble but dispersible. Other low HLB surfactants include but are not limited to PEG-6 glyceryl monooleate (HLB of about 3 or 4), and propylene glycol laurate (HLB of 4).

Tween™ hydrophilic surfactants (Polysorbates) are a family of PEG sorbitan esters (polyoxyethylene-sorbitan-fatty acid esters), for example mono-and tri-lauryl, palmityl, stearyl and oleyl esters of the type known and commercially available under the trade name Tween™ (Fiedler, H. P., "Lexikon der Hilfsstoffe fur Pharmazie, Kosmetic und Angrenzende Gebiete", Editio Cantor. D-7960 Aulendorf, 3rd edition, 1989, pages 1300–1304). Tween™ 20 (polyoxyethylene(20)sorbitan monolaurate) has an HLB of 16.7. Other types of Tween™ surfactants may also be useful for the compositions of the present invention.

Tween™ surfactants are soluble in water but not in oil. The chemical structure of this family of surfactants features one, two or three short PEG chains, generally of about 5 to 20 ethylene glycol units, connected by an ester bond to sorbitan. These surfactants are produced by various companies (Croda, ICI, Sandoz, Mazer, Atlas) and may appear under various trade names, besides Tween™: Sorlate™, Monitan™, Crillet™ and so forth. Members of this family which are polysorbates 20, 21, 0, 60, 61, 65, 80 and 85 have an HLB between 11 and 16.7, and therefore would be suitable for the present invention as high HLB surfactants.

Other suitable high HLB surfactants may be obtained from manufacturers such as Gattefosse Ltd., and include but are not limited to, sucrose fatty acid esters such as saccharose monopalmitate (HLB of 15) and saccharose monostearate (HLB of 11), or PEG-32 glyceryl laurate (HLB of 14). Suitable high HLB nonionic surfactants are polyethylene glycol (PEG) n-alkanol esters of the Brij family such as Brij 35, 56, 58, 76, 78, and 99 which have an HLB in the range of 12.4 to 16.9. Brij 56 is polyoxyethylene[10] cetyl ether and is an example of such a high HLB surfactant which can be substituted for Tween™ 20 or Cremophor™. Brij 56 has an HLB of 12.9.

Phospholipid (optional)

Next, various optional ingredients should be selected. One example of an optional ingredient is a phospholipid. A phospholipid is a phosphorylated diacylglyceride molecule or its derivative. The parent structure is diacylglycerol phosphate, or phosphatidic acid. Phosphatidyl choline (lecithin) is the choline ester of phosphorylated diacylglyceride. Synthetic lecithin are available with acyl chain lengths ranging from 4 to 19 carbons. The preferred lecithins for biological applications are those with alkyl chain lengths in the biological range (10 to 18 carbons). Naturally occurring lecithin can be obtained from a variety of sources such as egg, bovine heart, or soy bean. Unsaturated lecithins (dioleoyl; dilinoleoyl; alpha-palmitoyl, beta oleoyl; alpha palmitoyl, beta linoleoyl; and alpha oleoyl, beta palmitoyl), dianachidonyl lecithin (highly unsaturated and a prostaglandin precursor), and alpha palmito beta myristoyl lecithin are also available.

Certain phospholipids, such as phosphatidic acid, phosphatidyl serine, phosphatidyl inositol, cardiolipin (diphosphatidyl glycerol), and phosphatidyl glycerol, can react with calcium in serum, causing aggregation or the binding of liposheres to cell membranes. These unfavorable reactions can be minimized by combining these phospholipids with non-calcium binding phospholipids such as phosphatidylcholine. Phosphatidic acid can be isolated from egg or prepared synthetically (dimyristoyl, dipalmitoyl and distearoyl derivatives are available from Calbiochem). Bovine phosphatidyl serine is also available commercially (Sigma Chemical Co.. St. Louis, Mo.). Phosphatidyl inositol can be isolated from plant or bovine sources. Cardiolipin can be purified from bovine or bacterial sources. Phosphatidyl glycerol can also be purified from bacterial sources or prepared synthetically.

Phosphatidyl ethanolamine in the pure state self-aggregates in a calcium-independnt fashion, and is believed to have strong tendencies to aggregate with cell membranes, should be used in combination with non-aggregating phospholipids. Phosphatidyl ethanolamine is commercially available, isolated from egg, bacteria, bovine, or plasmalogen or as the synthetic dioctadecanoyl, dioleoyl, dihexadecyl, dilauryl, dimyristoyl and dipalmitoyl derivatives.

Ethoxylated Fat (optional)

Another optional ingredient is an ethoxylated fat. These ethoxylated fats may be reaction products of a natural or hydrogenated castor oil and ethylene oxide. The natural or hydrogenated castor oil may be reacted with ethylene oxide in a molar ratio of from about 1:35 to about 1:60, with optional removal of the polyethyleneglycol component from the products.

One example of a particularly preferred suitable, commercially available ethoxylated fat is Cremophor™ EL, which is one of a group of polyethyleneglycol-hydrogenated castor oils. Other members of this group, such as Cremophor™ RH 40 and Cremophor™ RH 60, may also be suitable.

Similar or identical products which may be used are available under the trade names NIKKOL (e.g. NIKKOL HCO-40 and HCO-60), MAPEG (e.g. MAPEG CO-40h), INCROCAS (e.g. INCROCAS 40) and TAGAT (for example polyoxyethylene-glycerol-fatty acid esters such as TAGAT RH 40; and TAGAT TO, a polyoxyethylene-glycerol-trioleate having an HLB value of 11.3).

Fatty Acid Ester (optional)

Yet another optional ingredient is a fatty acid ester such as tricaprin. Tricaprin is a hydrophobic triester of glycerol and caproic acid. Tricaprin does not dissolve in water and thus remains as a component of the dispersed cyclosporin-loaded particles after dispersion in aqueous solution. Tricaprin solubilizes cyclosporin in a fatty medium which is dispersed by the hydrophilic-hydrophobic dispersing agents. Other such fatty components which are suitable as replacement for tricaprin include, but are not limited to, pure and mixed alkyl esters of fatty acids and mixtures thereof. Examples include but are not limited to ethyl esters of fatty acids such as ethylstearate and ethylpalmitate triglycerides such as trilaurin and trimyristin. Mixtures of fats include hydrogenated vegetable oils. The preferred fats are those that solubilize cyclosporin with a melting point between 25 and 37° C. such that the resultant preconcentrate formulation forms a nanodispersion of solid particles which melt into an emulsion at body temperature.

The following specific examples illustrate various aspects of the present invention, and are not intending to be limiting in any way. For all experiments described below, unless otherwise stated, the particle size of the preconcentrate was measured with an N4-Coulter particle size analyzer, suitable for submicron particle size determination. Three drops of the preconcentrate were added to five milliliters of water. The particle size of the preconcentrate did not change when the preconcentrate was dispersed in five milliliters of 0.1N HCl solution. The member of the cyclosporin class which was used for the experiments described below was Ciclosporin (Cyclosporin A).

EXAMPLE 1

Effect of Solvent on Particle Size

An exemplary composition containing Ciclosporin, solvent, TRC (tricaprin), egg phospholipid (Avanti, USA), Tween™ 20, Span™ 80 and Cremophor™ was prepared with increasing amounts of ethyl lactate or N-methylpyrrolidone, as given in Table 1 (all amounts of ingredients are given in milligrams). The effect of adding increasing amounts of these ingredients to the composition of the present invention on (mean) particle size is also given in Table 1. Briefly, all compositions which contained either ethyl lactate or N-methylpyrrolidone had a particle size of less than 100 nm. The particle size decreased as the amount of either ethyl lactate or N-methylpyrrolidone was increased. Ethyl lactate was generally more effective than N-methylpyrrolidone for providing particles of a smaller size. The addition of ethylene glycol (as in Formulation 9), propylene glycol or liquid polyethylene glycol (PEG 200-600) to the formulations containing either ethyl lactate or N-methylpyrrolidone did not increase the particle size to greater than 100 nm.

TABLE 1

Effect of Solvent on Particle Size

| Ingredient | Formulation Number | | | | | | | | |
| --- | --- | --- | --- | --- | --- | --- | --- | --- | --- |
| | 1 | 2 | 3 | 4 | 5 | 6 | 7 | 8 | 9 |
| Ciclosporin | 100 | 100 | 100 | 100 | 100 | 100 | 100 | 100 | 100 |
| ethyl lactate | 0 | 100 | 200 | 400 | 0 | 0 | 100 | 200 | 200 |
| N-methyl pyrrolidone | 0 | 0 | 0 | 0 | 200 | 400 | 100 | 200 | 200 |
| phospholipid | 70 | 70 | 70 | 70 | 70 | 70 | 70 | 70 | 70 |
| Tween 20 | 270 | 270 | 270 | 270 | 270 | 270 | 270 | 270 | 270 |
| TRC | 130 | 130 | 130 | 130 | 130 | 130 | 130 | 130 | 130 |
| Span 80 | 100 | 100 | 100 | 100 | 100 | 100 | 100 | 100 | 100 |
| Cremophor EL | 300 | 300 | 300 | 300 | 300 | 300 | 300 | 300 | 300 |
| particle size | 189 | 92 | 42 | 28 | 82 | 57 | 88 | 39 | 31 |

EXAMPLE 2

Effect of Surfactant on Particle Size

An exemplary composition containing Ciclosporin, egg phospholipid (95% pure from Avanti, USA), ethyl lactate as a solvent, Tween™ 20 and Cremophor™ was prepared with increasing amounts of Span™ 80, as given in Table 2 (all amounts of ingredients are given in milligrams). The effect of adding increasing amounts of Span™ 80 to the composition of the present invention on (mean) particle size is also given in Table 2. Briefly, the compositions provided a liquid solution. When dispersed in deionized water, all compositions which contained Span™ 80 had a particle size of less than 100 nm. The particle size decreased as the amount of Span™ 80 was increased.

TABLE 2

Effect of Surfactant on Particle Size

| Ingredient | Formulation Number | | | | |
|---|---|---|---|---|---|
| | 1 | 2 | 3 | 4 | 5 |
| Ciclosporin | 100 | 100 | 100 | 100 | 100 |
| ethyl lactate | 300 | 300 | 300 | 300 | 300 |
| phospholipid | 50 | 50 | 50 | 50 | 50 |
| Tween 20 | 200 | 200 | 200 | 200 | 200 |
| Span 80 | 0 | 50 | 100 | 200 | 300 |
| Cremophor EL | 400 | 400 | 400 | 400 | 400 |
| particle size | 155 | 88 | 54 | 32 | 28 |

EXAMPLE 3

Effect of Other Ingredients on Particle Size

Different compositions containing Ciclosporin were prepared as described in Table 3 (all amounts of ingredients are given in milligrams). The effect of these ingredients on the particle size of the preconcentrate solution when dispersed in water is also given in Table 3. Briefly, compositions which had both low and high HLB surfactants (such as Tween™ or Cremophor™ and Span™) had a particle size of less than 100 nm. Tween and Cremophor can be substituted for each other as high HLB solvents (HLB>10) but a certain amount of either surfactant is required to obtain a suitable particle size, depending upon the quantities of the other components. In addition, the presence of a solvent such as ethyl lactate is required. A lipid such as tricaprin is clearly preferred. The presence of a phospholipid is also preferred to obtain a particle size in the range of 30 nm, although the particle size remained below 100 nm even without the phospholipid, as for Formulation 3, in which no phospholipid was added but the particle size was 95 nm.

TABLE 3

Effect of Other Ingredients on Particle Size

| Ingredient | Formulation Number | | | | | | | | | |
|---|---|---|---|---|---|---|---|---|---|---|
| | 1 | 2 | 3 | 4 | 5 | 6 | 7 | 8 | 9 | 10 |
| Ciclosporin | 100 | 100 | 100 | 100 | 100 | 100 | 100 | 100 | 100 | 100 |
| ethyl lactate | 400 | 200 | 400 | 400 | 400 | 400 | 400 | 600 | 400 | 400 |
| phospholipid | 100 | 100 | 0 | 100 | 100 | 100 | 100 | 100 | 100 | 100 |
| Tween 20 | 200 | 200 | 200 | 200 | 0 | 200 | 200 | 200 | 400 | 0 |
| TRC | 200 | 200 | 200 | 200 | 200 | 0 | 200 | 200 | 200 | 200 |
| Span 80 | 200 | 200 | 200 | 0 | 200 | 200 | 200 | 200 | 200 | 200 |
| Cremophor EL | 200 | 200 | 200 | 200 | 200 | 200 | 0 | 200 | 0 | 400 |
| particle size | 28 | 30 | 95 | 187 | 182 | 230 | 340 | 32 | 78 | 64 |

EXAMPLE 4

Effect of Low HLB Surfactant on Particle Size

Compositions containing Span™ 80 as an example of a low HLB surfactant was prepared by dissolving the components into a liquid at room temperature. The (mean) particle size is given in Table 4 (all amounts of ingredients are given in milligrams). Briefly, tricaprin could be substituted with other triglycerides and oil mixtures such as medium chain triglycerides (MCT). Brij is a group of polyoxyethylene alcohol ethers. Brij 56 is polyoxyethylene [10] cetyl ether and is a high HLB surfactant which can be substituted for Tween™ 20 or Cremophor. Brij™ 56 has an HLB of 12.9.

TABLE 4

Effect of High HLB Surfactant on Particle Size

| Ingredient | Formulation Number | | | | | | |
|---|---|---|---|---|---|---|---|
| | 1 | 2 | 3 | 4 | 5 | 6 | 7 |
| Ciclosporin | 100 | 100 | 100 | 100 | 100 | 100 | 100 |
| ethyl lactate | 400 | 400 | 400 | 400 | 0 | 400 | 400 |
| N-methyl pyrrolidone | 0 | 0 | 0 | 0 | 400 | 0 | 0 |
| phospholipid | 70 | 70 | 70 | 70 | 70 | 70 | 70 |
| Span 80 | 270 | 0 | 270 | 270 | 270 | 270 | 270 |
| Tween 20 | 0 | 270 | 270 | 0 | 0 | 0 | 270 |
| Brij 56 | 0 | 0 | 0 | 270 | 270 | 270 | 270 |
| TRC | 130 | 130 | 130 | 130 | 130 | 0 | 130 |
| MCT | 0 | 0 | 0 | 0 | 0 | 130 | 0 |
| Cremophor EL | 400 | 400 | 400 | 400 | 400 | 400 | 0 |
| particle size | 56 | 197 | 25 | 29 | 55 | 48 | 83 |

EXAMPLE 5

Selection of a First Preferred Formulation

Two of the preferred formulations, 5 and 8, were selected from the formulations in Table 5 (all amounts of ingredients are given in milligrams). An additional preferred formulation is given in Example 10. These formulations had the smallest particle size (in the range of about 30 nm).

TABLE 5

Preferred Formulations

| Ingredient | Formulation Number | | | | | | | |
|---|---|---|---|---|---|---|---|---|
| | 1 | 2 | 3 | 4 | 5 | 6 | 7 | 8 |
| Ciclosporin | 100 | 200 | 100 | 100 | 100 | 100 | 100 | 100 |
| ethyl lactate | 400 | 800 | 400 | 400 | 400 | 400 | 400 | 400 |
| phospholipid | 70 | 140 | 70 | 70 | 100 | 70 | 70 | 100 |
| Span 80 | 270 | 540 | 270 | 270 | 270 | 150 | 200 | 200 |
| Tween 20 | 270 | 540 | 270 | 270 | 270 | 150 | 200 | 200 |

TABLE 5-continued

Preferred Formulations

| Ingredient | Formulation Number | | | | | | | |
|---|---|---|---|---|---|---|---|---|
| | 1 | 2 | 3 | 4 | 5 | 6 | 7 | 8 |
| TRC | 130 | 260 | 130 | 130 | 200 | 130 | 130 | 200 |
| Cremophor EL | 400 | 800 | 100 | 200 | 0 | 0 | 0 | 0 |
| Cremophor HR | 40 | 0 | 0 | 0 | 200 | 200 | 200 | 200 |
| particle size | 41 | 55 | 68 | 42 | 23 | 75 | 52 | 29 |

EXAMPLE 6

Storage Stability of Preferred Formulation

One composition was prepared at two different total quantities (all amounts of ingredients are given in milligrams). At the first volume, the composition contained 400 Ciclosporin, 1600 ethyl lactate. 400 phospholipid, 800 Span™ 80,800 Tween 20,800 TRC and 800 Cremophor™ HR. At the second volume, the amount of each ingredient was ten-fold larger. Both compositions were easily prepared by dissolving all components to a liquid solution by mixing with mild heating (about 40° C.). Preferably, the phospholipid was first dissolved in ethyl lactate, and then all other components were added with continuous mixing, apart from Ciclosporin which was added last. The mean particle size of the composition was measured after dispersion of different amounts of the composition in deionized water by using the light scattering technique with a Coulter N4 particle size analyzer. Both volumes of the composition had a particle size below 30 nm which is preferred. This composition was used for human studies, as described in greater detail below.

TABLE 6

Dispersion in Water

| | Drops of composition/ml of water | | | |
|---|---|---|---|---|
| particle size | 3 drops/ 5 ml | 3 drops/ 5 ml | 10 drops/ 5 ml | 20 drops/ 5 ml |
| first test | 37 | 22 | 18 | 18 |
| second test | 22 | 21 | 17 | 17 |
| third test | 19 | 24 | 18 | 17 |

The stability of the composition was tested by loading doses of 50 mg of Ciclosporin into hard gelatin capsules (size 00) or in glass containers, and then storing the composition at room temperature (25° C.) or at refrigeration (4° C.). The particle size and the Ciclosporin content was determined after 3 and 6 months of storage. All samples were found to have a particle size in the range between 17.2 and 32.6 at any dispersion range (3 to 20 drops per 5 ml). As calculated from the peak size after analysis by HPLC (high pressure liquid chromatography), the Ciclosporin content for all stored formulations was in the range of 95 to 104% of the initial concentration.

EXAMPLE 7

Analysis of Preferred Formulation

The composition of Example 6 was prepared 5 times independently for 400 mg Ciclosporin. The particle size. Ciclosporin content, the morphology of the formed particles and the melting point of the particles was determined. The bioactivity of the Ciclosporin formulation on T-cells was also determined.

The particle size of all formulations ranged between 18 to 29 nm when dispersed in deionized water or 0.1 N HCl solution. The particles were viewed by Transmission Electron Microscope (TEM) at high magnification. Spherical particles with a narrow size distribution in the range of 30 nm were observed. The melting point of the particles was determined by differential scanning calorimeter (DSC) and was found to be in a temperature range of from 30 to 35° C. The composition was highly effective at inhibiting the activity of T-cells. The results clearly indicate the superior stability, reproducibility and efficacy of the preferred formulation.

EXAMPLE 8

Effect of Ciclosporin Content on Preferred Formulation

The composition of Example 6 was prepared with increasing amounts of Ciclosporin and the particle size was determined. The results, shown in Table 7, are an average of five independent experiments (all amounts of ingredients are given in milligrams). The particle size increases as the amount of Ciclosporin is increased above 60 mg in this composition.

TABLE 7

Effect of Ciclosporin

| Ingredient | Formulation Number | | | | | |
|---|---|---|---|---|---|---|
| | 1 | 2 | 3 | 4 | 5 | 6 |
| Ciclosporin | 50 | 55 | 60 | 65 | 70 | 75 |
| ethyl lactate | 200 | 200 | 200 | 200 | 200 | 200 |
| phospholipid | 50 | 50 | 50 | 50 | 50 | 50 |
| Span 80 | 100 | 100 | 100 | 100 | 100 | 100 |
| Tween 20 | 100 | 100 | 100 | 100 | 100 | 100 |
| TRC | 100 | 100 | 100 | 100 | 100 | 100 |
| Cremophor HR | 100 | 100 | 100 | 100 | 100 | 100 |
| particle size | 28 | 31 | 30 | 56 | 88 | 92 |

The composition containing 50 mg of Ciclosporin was bottled. The bottles were stored at room temperature or at 37° C. and the particle size was determined. The results are shown in Table 8.

TABLE 8

Stability of Ciclosporin Compositions

| Day No. | Particle size (room temp) | Particle size (37° C.: nm) |
|---|---|---|
| 0 | 30 | 30 |
| 7 | 67 | 24 |
| 13 | 39 | 26 |
| 16 | 65 | 33 |
| 42 | 59 | 33 |
| 52 | 31 | 28 |
| 4.3 months | 20.9 | 17.1 |
| 7 months | 29.2 | 33.7 |
| 7.6 months | 26.4 | 27.5 |
| 9 months | 29.8 | 31.2 |

EXAMPLE 9

Pharmacokinetic Human Studies

A randomized pilot pharmacokinetic study was undertaken to investigate the pharmacokinetic performance of the composition of the present invention, when compared to the standard commercially available formulation for Ciclosporin (Sandimmune Neoral™, Sandoz A.G.). The formulation of the present invention was tested in capsules containing 50 mg of Ciclosporin. The standard composition was tested with soft gelatin capsules containing 100 mg Ciclosporin. Four capsules of the formulation of the present invention, containing 50 mg of Ciclosporin per capsule, or two capsules of the commercially available formulation, containing 100 mg of Ciclosporin per capsule, were orally administered to six fasting volunteers, for a total dosage of 200 mg of Ciclosporin. Blood samples were then drawn as follows: 0, 0.25, 0.5, 0.75, 1, 1.5, 2, 2.5, 3, 3.5, 4, 4.5, 5, 6, 9, 12, 15 and 24 hours post administration. A one-week washout period separated the two study periods. Plasma concentrations of Ciclosporin were determined by using a standard Tdx method used for monitoring patients receiving Ciclosporin. A curve of concentration vs, time was constructed for each volunteer for each period, as shown in FIG. 1 and described in greater detail below. The observed maximal concentration was recorded as Cmax and the area under the curve, AUC, was calculated for each volunteer.

The following formulation of the present invention was studied:

| Ingredient | Weight per capsule (mg) | Total weight (g) |
| --- | --- | --- |
| Ciclosporin | 50 | 0.25 |
| ethyl lactate | 200 | 0.100 |
| Egg phosphatidylcholine | 50 | 0.25 |
| Span 80 | 100 | 0.050 |
| Tween 20 | 100 | 0.050 |
| TRC | 100 | 0.050 |
| Cremophor HR | 100 | 0.050 |
| total: | 700 | 0.350 |

The composition was prepared as follows. Ciclosporin, egg phosphatidylcholine and tricaprin were dissolve in a solution of ethyl lactate and Tween™ 20 by mixing in a beaker at room temperature. The other ingredients were added and mixed to form a clear yellowish liquid. The clear liquid solution (0.350 g) was placed into 500 hard gelatin capsules (size 00). About 10 capsules were taken for particle size determination and Ciclosporin content. Each capsule contained 700 mg solution (weight range: 665–735 mg) with the corresponding amount of Ciclosporin (47.5 to 52.5 mg/capsule). The particle size of the formulation after dispersion of the contents of one capsule in 10 ml of 0.1 N HCl solution or in deionized water was determined with light scattering by using the N4 particle size analyzer (Coulter). The almost clear dispersion had an average particle size of 28 nm.

The results of the test on human volunteers are shown in Table 9 below.

TABLE 9

Test on Human Subjects

| Formulation | AUC (ng × hour/ml) | Cmax (ng/ml) | Tmax (hours) |
| --- | --- | --- | --- |
| present invention (n = 6) | 5555 ± 842 (4771–7147) | 1328 ± 216 (990–1591) | 1.67 ± 0.28 (1–3) |
| standard (n = 4) | 5221 ± 2200 (2806–7784) | 1100 ± 259 (790–1405) | 1.88 ± 0.24 (1.5–2.5) |

The presented values for all pharmacokinetic parameters are mean ±S.D. and the values in parentheses are the range. The number of volunteers participating in the study is given as n. The average blood levels are shown in FIG. 1. FIG. 1 is a graph of Ciclosporin blood concentration after oral administration of 4 capsules of 50 mg Ciclosporin in the dispersible concentrate formulation of the invention. The formulation included 50 mg Ciclosporin, 200 mg ethyl lactate, 50 mg egg phospholipid, 100 mg Tween™ 20, 100 mg TRC, 100 mg Span™ 80, and 100 mg Cremophor™, for a resultant particle size after dispersion of 28 nm. As a reference, two Sandimmun Neoral™ (Sandoz) capsules, containing 100 mg Ciclosporin total, were administered as a reference. The results shown in FIG. 1 are an average of n=6 for the formulation of the present invention and n=4 for the commercially available formulation. Sandimmun Neoral™ (Sandoz).

This human study clearly indicates the efficacy of the formulation of the present invention as compared to the best commercially available formulation. Sandimmun Neoral™ (Sandoz). The formulation of the present invention is clearly superior to this commercially available formulation as it provided a higher Cmax and AUC, with a significantly narrower standard deviation, indicating a lesser degree of variation between individual subjects.

EXAMPLE 10

Pharmacokinetic Human Studies for a Second Preferred Composition

A randomized pilot pharmacokinetic study was undertaken to investigate the pharmacokinetic performance of a second preferred composition of the present invention, when compared to the standard commercially available formulation for Ciclosporin (Sandimmune Neoral™, Sandoz A.G.). This second preferred formulation is a concentrated formulation with a higher load of cyclosporin as compared to the formulation of Example 9, containing about twenty percent more cyclosporin.

The following formulation of the present invention was studied:

| Ingredient | Weight per capsule (mg) | Total weight (Kg) |
| --- | --- | --- |
| Ciclosporin | 100 | 1 |
| ethyl lactate | 332 | 3.32 |
| lecithin (soy phospholipid) | 84 | 0.84 |
| sorbitan monooleate (Span 80) | 168 | 16.8 |
| polysorbate 20 (Tween 20) | 168 | 16.8 |
| Cremophor RH 40 | 168 | 16.8 |
| triglyceride (tricaprin) | 168 | 16.8 |
| total: | 1188 | 11.88 |

The composition was prepared as for the composition of Example 9. The particle size of the formulation after dispersion of the contents of one capsule in 10 ml of 0.1 N HCl solution or in deionized water was determined using the N4 particle size analyzer (Coulter). The almost clear dispersion had an average particle size of 25–50 nm.

Figure 2:
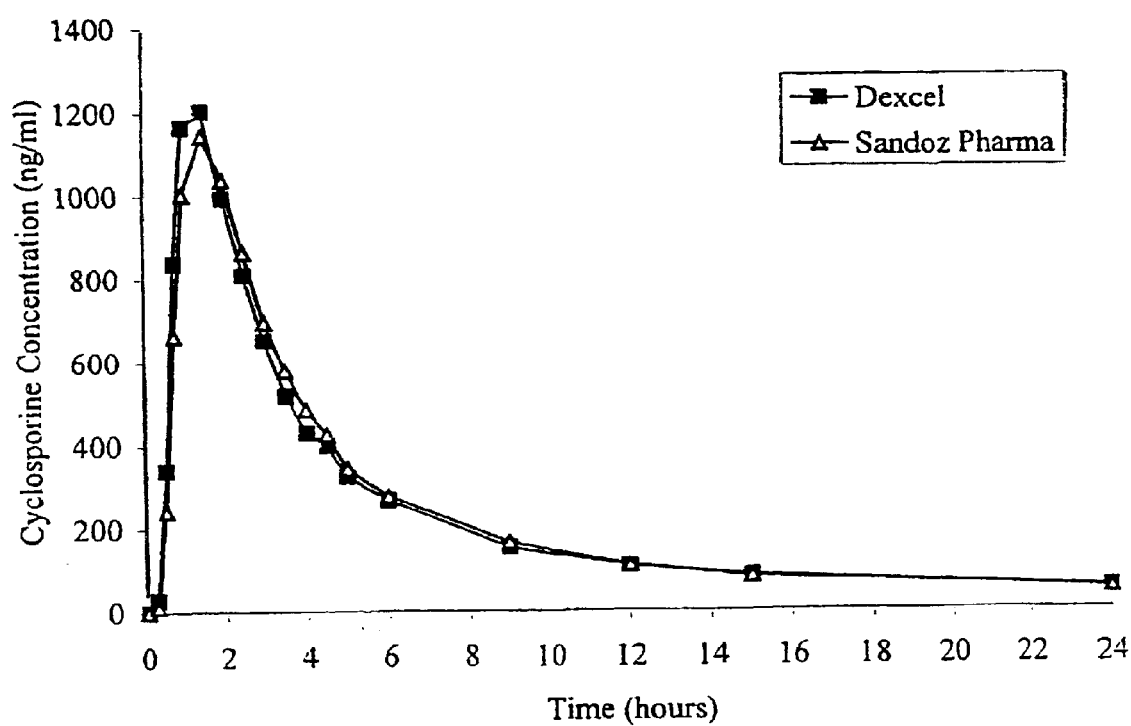
FIG. 2 is a graph of cyclosporin blood concentration after oral administration of 2 capsules of 100 mg cyclosporin in a second dispersible concentrate formulation of the invention.

This second preferred formulation of the present invention was tested in human volunteers with soft gelatin capsules containing 100 mg of Ciclosporin. The standard composition was tested with soft gelatin capsules containing 100 mg Ciclosporin. Two capsules of the formulation of the present invention, containing 100 mg of Ciclosporin per capsule, or two capsules of the commercially available formulation, containing 100 mg of Ciclosporin per capsule, were orally administered to twelve fasting volunteers, for a total dosage of 200 mg of Ciclosporin in twelve volunteers. Blood samples were then drawn as follows: 0, 0.25, 0.5, 0.75, 1, 1.5, 2, 2.5, 3, 3.5, 4, 4.5, 5, 6, 9, 12, 15 and 24 hours post administration. A one-week washout period separated the two study periods. Plasma concentrations of Ciclosporin were determined by using a standard TDX method used for monitoring patients receiving Ciclosporin. A curve of concentration vs, time was constructed for each volunteer for each period, as shown in FIG. 2 and described in greater detail below. The observed maximal concentration was recorded as Cmax, the time of observing this concentration was recorded as Tmax, and the area under the curve, AUC, was calculated for each volunteer.

The presented ratios of AUC and Cmax are geometric means of the individual ratios, after being calculated both directly and through logarithmic transformation (multiplicative model), according to preferred methods for determining pharmokinetics. The 90% parametric (ANOVA) Confidence Intervals were computed for all ratios.

The results of the test on human volunteers are shown in Table 10 below.

TABLE 10

Test on Human Subjects

| Formulation | AUC (ng × hour/ml) | Cmax (ng/ml) | Tmax (hours) |
|---|---|---|---|
| present invention (n = 12) | 5511.17 ± 1455.74 (3108.43–7622.71) | 1265.17 ± 262.94 (733.8–1779.4) | 6.00 ± 1.60 (4–8) |
| standard (n = 12) | 5552.06 ± 984.9 (3094.14–6596.89) | 1281.51 ± 323.11 (777–1881) | 7.13 ± 3.04 (4–12) |
| ratio (90% ANOVA CI) | 0.97 (0.89–1.06) | 1.00 (0.92–1.08) | |
| difference (range) | | | −0.25 ± 0.40 (−1.0–0.5) |

The presented values for all pharmacokinetic parameters are mean ±S.D. and the values in parentheses are the range. The number of volunteers participating in the study is given as n. The ratio is the geometric means of the ratios for AUC and Cmax as calculated directly or through logarithmic transformation, as previously described. The difference is the mean result and range of Tmax.

The average blood levels are shown in FIG. 2. FIG. 2 is a graph of Ciclosporin blood concentration after oral administration of 2 capsules of 100 mg Ciclosporin in the second preferred dispersible concentrate formulation of the invention. Two Sandimmun Neoral™ (Sandoz) capsules, containing 100 mg Ciclosporin total, were administered as a reference. The results shown in FIG. 2 are an average of n=12 for the formulation of the present invention and for the commercially available formulation, Sandimmun Neoral™ (Sandoz).

This human study clearly indicates the efficacy of the formulation of the present invention as compared to the best commercially available formulation, Sandimmun Neoral™ (Sandoz). The formulation of the present invention is clearly bioequivalent to this commercially available formulation as the extent and rate of absorption were similar.

In particular, the AUC values, showing the extent of absorption, had a ratio of 0.97 with a 90% ANOVA confidence interval (CI) of 0.89–1.06, which supports the bioequivalence of these formulations. Similarly, the Cmax values, showing the rate of absorption, had a ratio of 1.00, with a 90% ANOVA confidence interval of 0.92–1.08, which also supports the bioequivalence of these formulations. The rate of absorption as shown by the Tmax values also supports bioequivalence, as there was only a difference of −0.25 hours between the Tmax values of these formulations, with a range of −1.0 to 0.5 hours. Thus, clearly the second preferred formulation of the present invention was also shown to be bioequivalent to the standard, commercial available formulation, as for the composition of the present invention of Example 9.

EXAMPLE 11

Effect of Fatty Acid Ester on Particle Size

An exemplary composition containing Ciclosporin, ethyl lactate, egg phospholipid (Avanti, USA), and Tween™ 20 was prepared with increasing amounts of TRC (tricaprin), as given in Tables 11A and B (all amounts of ingredients are given in milligrams). The effect of adding increasing amounts of TRC to the composition of the present invention on (mean) particle size is also given in Tables 11A and B.

Briefly, none of the compositions had a particle size of less than 100 nm. The best compositions in terms of particle size were composition number one, which featured 300 mg TRC with 100 mg phospholipid; and composition number two, which features 200 mg TRC with 100 mg phospholipod. For the remaining compositions, in which TRC and/or phospholipid was reduced in amount or absent, had inferior particle sizes. The addition of corn oil in place of TRC caused two layers to form, due to the insolubility of corn oil in ethyl lactate, such that particle size could not be measured. Table 11A shows the effect of TRC on particle size for a single batch of each formulation, but with the particle size measured twice and with both values given separately. Table 11B shows the effect of TRC on particle size for multiple versions of formulation number two, again with the particle size measured twice and with both values given separately.

TABLE 11A

Effect of TRC on Particle Size

| | Formulation Number | | | | | | | | |
|---|---|---|---|---|---|---|---|---|---|
| Ingredient | 1 | 2 | 3 | 4 | 5 | 6 | 7 | 8 | 9 |
| Ciclosporin | 150 | 150 | 150 | 150 | 0 | 150 | 150 | 150 | 150 |
| ethyl lactate | 600 | 600 | 600 | 600 | 600 | 600 | 600 | 600 | 600 |
| phospholipid | 100 | 100 | 100 | 100 | 100 | 0 | 0 | 0 | 0 |
| Tween 20 | 400 | 400 | 400 | 400 | 400 | 400 | 400 | 400 | 600 |
| TRC | 300 | 200 | 100 | 0 | 300 | 300 | 0 | 0 | 0 |
| corn oil | 0 | 0 | 0 | 0 | 0 | 0 | 0 | 300 | 200 |

TABLE 11A-continued

Effect of TRC on Particle Size

| Ingredient | Formulation Number | | | | | | | | |
|---|---|---|---|---|---|---|---|---|---|
| | 1 | 2 | 3 | 4 | 5 | 6 | 7 | 8 | 9 |
| particle size | 150 | 148 | 152 | 179 | 162 | 217 | 208 | ND | ND |
| | 170 | 166 | 166 | 166 | 160 | 231 | 257 | | |

TABLE 11B

Effect of TRC on Particle Size

| Ingredient | Formulation Number | | |
|---|---|---|---|
| | 2a | 2b | 2c |
| Ciclosporin | 150 | 150 | 150 |
| ethyl lactate | 600 | 600 | 400 |
| phospholipid | 100 | 50 | 50 |
| Tween 20 | 600 | 600 | 600 |
| TRC | 200 | 200 | 200 |
| particle size | 145 | 199 | 155 |
| | 172 | 207 | 272 |

EXAMPLE 12

Effect of Hydrophilic Solvent on Particle Size

Different compositions containing Ciclosporin were prepared as described in Tables 12A and B (all amounts of ingredients are given in milligrams). The effect of two different hydrophilic solvents, ethyl lactate and 1,2 propylene glycol, on the particle size of the preconcentrate solution when dispersed in water is also given in Table 12A; while the effect of three such solvents, ethyl lactate, glycofurol and N-methyl pyrrolidone, is given in Table 12B. Propylene glycol and glycofurol are both hydrophilic solvents which are frequently used in background art cyclosporin compositions and which are well known in the art.

Briefly, compositions which included propylene glycol and/or which did not include ethyl lactate had much higher particle sizes than compositions which only included ethyl lactate. Ethyl lactate and glycofurol gave similar results, as compositions featuring one of these solvents had small particle sizes (less than 100 nm). Furthermore, clearly the lack of Span™ 80 is disadvantageous for these formulations, as shown by the relatively larger particle sizes.

TABLE 12A

Effect of Hydrophilic Solvent on Particle Size

| Ingredient | Formulation Number | | | | | | | |
|---|---|---|---|---|---|---|---|---|
| | 1 | 2 | 3 | 4 | 5 | 6 | 7 | 8 |
| Ciclosporin | 100 | 100 | 100 | 100 | 100 | 100 | 100 | 100 |
| ethyl lactate | 400 | 200 | 0 | 0 | 0 | 400 | 0 | 360 |
| 1,2-propylene glycol | 0 | 0 | 0 | 400 | 0 | 0 | 400 | 0 |
| phospholipid | 70 | 70 | 70 | 70 | 70 | 70 | 70 | 0 |
| Tween 80 | 270 | 270 | 270 | 270 | 270 | 270 | 270 | 0 |
| TRC | 130 | 130 | 130 | 130 | 0 | 0 | 0 | 0 |
| MCT | 0 | 0 | 0 | 0 | 160 | 160 | 140 | 160 |
| Cremophor EL | 0 | 330 | 330 | 330 | 400 | 400 | 500 | 380 |
| particle size | 189 | 141 | 95 | 298 | 182 | 125 | 160 | 239 |

TABLE 12B

Effect of Hydrophilic Solvent on Particle Size

| Ingredient | Formulation Number | | | | | |
|---|---|---|---|---|---|---|
| | 1 | 2 | 3 | 4 | 5 | 6 |
| Ciclosporin | 100 | 100 | 100 | 100 | 100 | 100 |
| ethyl lactate | 400 | 300 | 0 | 0 | 400 | 400 |
| glycofurol | 0 | 0 | 400 | 0 | 0 | 0 |
| N-methyl pyrrolidone | 0 | 0 | 0 | 400 | 0 | 0 |
| phospholipid | 50 | 50 | 50 | 50 | 50 | 100 |
| Span 80 | 200 | 200 | 200 | 200 | 270 | 200 |
| Tween 20 | 200 | 200 | 200 | 200 | 270 | 200 |
| TRC | 200 | 200 | 200 | 200 | 200 | 200 |
| Cremophor HR 40 | 200 | 200 | 200 | 200 | 200 | 200 |
| particle size | 94.8 | 42.1 | 25.2 | 111 | 86 | 30.1 |

EXAMPLE 13

Effect of Ciclosporin Concentration on Particle Size

Different compositions containing Ciclosporin were prepared as described in Table 13 (all amounts of ingredients are given in milligrams). The effect of different concentrations of Ciclosporin on the particle size of the preconcentrate solution when dispersed in water is also given in Table 13. The preferred formulation which was used for the second human bioavailability trial is formulation number two (Table 13).

Briefly, relatively high concentrations of Ciclosporin, up to 140 mg, still resulted in formulations with small particle sizes (less than 100 nm). However, the best results were obtained with concentrations of less than 100 mg of Ciclosporin.

TABLE 13

Effect of Ciclosporin Concentration on Particle Size

| Ingredient | Formulation Number | | | | |
|---|---|---|---|---|---|
| | 1 | 2 | 3 | 4 | 5 |
| Ciclosporin | 100 | 120 | 130 | 140 | 160 |
| ethyl lactate | 400 | 400 | 400 | 400 | 400 |
| phospholipid | 100 | 100 | 100 | 100 | 100 |
| Span 80 | 200 | 200 | 200 | 200 | 200 |
| Tween 20 | 200 | 200 | 200 | 200 | 200 |
| TRC | 200 | 200 | 200 | 200 | 200 |
| Cremophor RH 40 | 200 | 200 | 200 | 200 | 200 |
| particle size | 33.3 | 40.6 | 44 | 82.9 | 92.1 |

EXAMPLE 14

Stability Testing of the Formulations of the Present Invention

The preferred formulation according to the present invention for high loading of cyclosporin was examined for storage stability characteristics. The tested formulation is given below in Table 14A, while the results of the stability tests are given in Table 14B. Briefly, the formulation according to the present invention showed good storage stability under accelerated storage conditions.

In addition, these experiments demonstrate that storage stability, and the resultant effect of prolonged storage on formulations according to the present invention, can optionally be determined by measuring the particle size as previously performed. Once the particle size has been shown to be increased over a predetermined limit, the composition is then preferably determined to have destabilized beyond an acceptable limit and to no longer be suitable for administration to a subject.

The tested formulation is shown in Table 14A below, and is the preferred formulation according to the present invention for a concentrated, high load cyclosporin formulation.

TABLE 14A

| Ingredient | Amount (mg) |
| --- | --- |
| Ciclosporin | 120 |
| Ethyl lactate | 400 |
| Phospholipid | 100 |
| Tween 20 | 200 |
| Span 80 | 200 |
| Cremophor RH 40 | 200 |
| Tricaprin | 200 |

The stability testing was performed under accelerated storage conditions of 40° C. and 75% relative humidity for up to three months, which is approximately equivalent to eighteen months of room temperature storage (Table 14B).

TABLE 14B

| | | Accelerated storage | | | |
| --- | --- | --- | --- | --- | --- |
| Test performed | Specification | Initial Test | 1 Month | 2 Months | 3 Months |
| cyclosporin average content (percentage) | 95–105 mg | 98.4 | 98.1 | 100.7 | 97.1 |
| particle size | 100 nm | 21.3 | 27.5 | 24.3 | 29.2 |

EXAMPLE 15

Effect of Cyclosporin Concentration on Particle Size Distribution

A preferred formulation according to the present invention was tested for the effect of cyclosporin concentration on particle size for scaled-up batches of the composition (10,000 capsules). The amount of cyclosporin was held constant, while the remaining ingredients were adjusted in order to provide increasingly diluted formulations. The particle size was measured as previously described. Briefly, although all formulations had a suitable particle size of less than about 100 nm, clearly the more diluted formulations had a lower, and hence more desirable, particle size. The three tested formulations and results thereof are given in Table 15 below.

TABLE 15

| Ingredient | formulation 1 | formulation 2 | formulation 3 |
| --- | --- | --- | --- |
| Ciclosporin | 50 | 50 | 50 |
| Tween 20 | 72 | 84 | 100 |
| Span 80 | 72 | 84 | 100 |

TABLE 15-continued

| Ingredient | formulation 1 | formulation 2 | formulation 3 |
| --- | --- | --- | --- |
| Egg Phosphatidylcholine | 36 | 42 | 50 |
| Tricaprin | 72 | 84 | 100 |
| Cremophor RH 40 | 72 | 84 | 100 |
| Ethyl lactate | 144 | 166 | 200 |
| particle size | 73.6 nm | 37.9 nm | 32.3 nm |

EXAMPLE 16

Effect of Particle Size on Bioavailability

Figure 3:
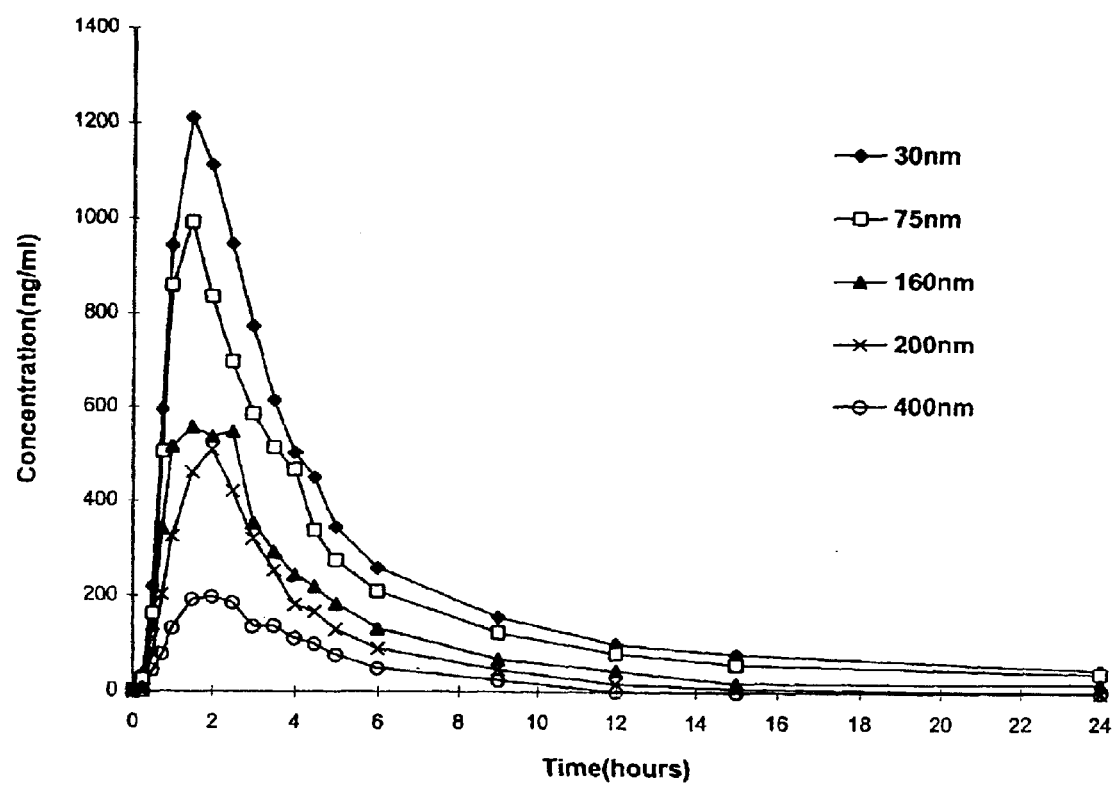
FIG. 3 is a graph of cyclosporin blood concentration after oral administration of formulations according to the present invention in order to demonstrate the effect of particle size on bioavailability.

The effect of particle size on bioavailability was tested with six formulations: the three formulations of Example 15, and three additional formulations, given in Table 16 below. Briefly, the formulations were administered to human volunteers and blood levels of cyclosporin were measured substantially as previously described. The resultant blood levels are shown in the graph of FIG. 3. The relationship between each symbol of the graph and the formulation number is as follows: solid circle (30 nm particle size), formulation number 3 of Table 15; open square (75 nm), formulation number 1 of Table 15; solid triangle (160 nm), formulation number 1 of Table 16; cross (200 nm), formulation number 2 of Table 16; and open circle (400 nm), formulation number 3 of Table 16.

As shown, the greatest bioavailability is seen with the smaller particle sizes, particularly 30 nm and 75 nm. A sharp drop in bioavailability is seen with particle sizes greater than 100 nm, such as for the formulations with 160 nm, 200 nm and 400 nm particle sizes. Thus, the particle size of the formulation should be less than about 100 nm, and is preferably even smaller.

TABLE 16

| Ingredient | formulation 1 | formulation 2 | formulation 3 |
| --- | --- | --- | --- |
| Ciclosporin | 50 | 50 | 50 |
| Tween 80 | 140 | 100 | 0 |
| Egg Phosphatidylcholine | 30 | 100 | 200 |
| Tricaprin | 100 | 100 | 100 |
| Ethyl lactate | 200 | 200 | 300 |
| particle size | 160 nm | 200 nm | 400 nm |

EXAMPLE 17

Effect of Various Ingredients on the Preferred Formulation of the Present Invention The effect of removing various ingredients from the formulation of the present invention was examined, in order to determinet the contribution of these individual ingredients to the overall particle size of the formulation. The concentration of at least one other ingredient was then increased in an attempt to stabilize the formulation in the absence of the missing ingredient. Table 17A shows the effect of removing Tween™ 20 and/or Span™ 80, or replacing tricaprin with corn oil. Table 17B shows the effect of Cremophor™ RH 40 alone, without Tween™ 20 or Span™ 80. The particle size was measured as previously described. Briefly, although the combination of Tween™ 20 and Span™ 80 is preferred, substituting sufficient amounts of Cremophor™ RH 40 can overcome the lack of such a surfactant combination. The particle size of the formulation was not measured with corn oil, since the corn oil separated from the other ingredients, such that particles were not formed.

TABLE 17A

| Ingredient (mg)    | 1            | 2          | 3            | 4   |
|--------------------|--------------|------------|--------------|-----|
| Ciclosporin        | 100          | 100        | 100          | 100 |
| Tween 20           | 170          | 170        | 0            | 170 |
| Span 80            | 170          | 0          | 170          | 170 |
| Lecithin           | 85           | 85         | 85           | 85  |
| TRC                | 170          | 170        | 170          | 0   |
| corn oil           | 0            | 0          | 0            | 170 |
| Cremophor RH 40    | 170          | 340        | 340          | 170 |
| ethyl lactate      | 335          | 335        | 335          | 335 |
| particle size (nm) | 23.4<br>59.1 | 171<br>180 | 36.6<br>34.6 | ND  |

TABLE 17B

| Ingredient (mg)    | 1   | 2   | 3    |
|--------------------|-----|-----|------|
| Ciclosporin        | 100 | 100 | 100  |
| Tween 20           | 0   | 0   | 0    |
| Span 80            | 0   | 0   | 0    |
| Lecithin           | 85  | 85  | 85   |
| TRC                | 170 | 170 | 170  |
| Cremophor RH 40    | 340 | 510 | 680  |
| Ethyl lactate      | 335 | 335 | 335  |
| particle size (nm) | 199 | 170 | 37.9 |

EXAMPLE 18

Methods of Administration of Cyclosporins

A cyclosporin, such as Ciclosporin, can be administered to a subject in a number of ways, which are well known in the art. Hereinafter, the term "subject" refers to the human or lower animal to whom cyclosporin was administered. For example administration may be done topically (including ophtalmically, vaginally, rectally, intranasally), orally, or parenterally, for example by intravenous drip or intraperitoneal, subcutaneous, or intramuscular injection.

Formulations for topical administration may include but are not limited to lotions, ointments, gels, creams, suppositories, drops, liquids, sprays and powders.

Compositions for oral administration include powders or granules, suspensions or solutions in water or non-aqueous media, sachets, capsules or tablets. Thickeners, diluents, flavorings, dispersing aids, emulsifiers or binders may be desirable. Compositions for oral administration preferably include a soft or hard gelatin capsule.

Formulations for parenteral administration may include but are not limited to sterile aqueous solutions which may also contain buffers, diluents and other suitable additives.

The formulations of the present invention may optionally be administered as a dispersible concentrate or as a dispersion in aqueous liquid. Alternatively, these formulations may be lyophilized (dried) after the formation of the dispersion in aqueous liquid. The lyophilized (dried) dispersion is also optionally administered to the subject. The preferred route of adminstration is oral administration.

Dosing is dependent on the severity of the symptoms and on the responsiveness of the subject to cyclosporin. Persons of ordinary skill in the art can easily determine optimum dosages, dosing methodologies and repetition rates.

EXAMPLE 19

Methods of Treatment with Cyclosporins

Cyclosporins are particularly noted for the treatment and prevention of organ or tissue transplant rejection, for the treatment and prevention of autoimmune disease and of inflammatory conditions, and for the treatment of multi-drug resistance (MDR).

With regard to the treatment and prevention of organ or tissue transplant rejection, the compositions of the present invention containing cyclosporin are useful for the treatment of the recipients of heart, lung, combined heart-lung, liver, kidney, pancreatic, bone-marrow, skin or corneal transplants, and in particular allogenic transplants, for example. In addition, the compositions of the present invention are useful for the prevention of graft-versus-host-disease, which can sometimes be seen following bone marrow transplantation.

With regard to the treatment and prevention of autoimmune disease and of inflammatory conditions, the compositions of the present invention containing cyclosporin may be useful for the treatment of autoimmune hematological disorder (including hemolytic anemia, aplastic anemia pure red cell anemia and idiopathic thrombocytopenia), systemic lupus erythematosus, polychondritis, scleroderma, Wegener granulamatosis, dermatomyositis, chronic active hepatitis, myasthenia gravis, psoriasis, Steven-Johnson syndrome, idiopathic sprue, autoimmune inflammatory bowel disease (such as ulcerative colitis and Crohn's disease), endocrine opthalmopathy, Graves disease, sarcoidosis, multiple sclerosis, primary billiary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, such as idiopathic nephrotic syndrome or minimal change nephropathy).

In addition, these compositions may be particularly useful for inflammatory conditions with an etiology including an autoimmune component such as arthritis (for example, rheumatoid arthritis, arthritis chronica progrediente and arthritis deformans) and rheumatic diseases.

With regard to multi-drug resistance (MDR), the compositions of the present invention containing cyclosporin may be useful for reversing or abrogating anti-neoplastic agent resistance in tumors and the like.

The following examples are illustrations only of methods of treating these disorders with the compositions of the present invention containing cyclosporin, and are not intended to be limiting.

The method includes the step of administering the composition of the present invention containing cyclosporin, as described in Example 18 above, to a subject to be treated. The composition of the present invention is administered according to an effective dosing methodology, preferably until a predefined endpoint is reached (if possible), such as the absence of symptoms of the disorder in the subject. For other disorders, such as organ or tissue transplant rejection, the composition of the present invention may need to be administered continuously without any endpoint.

Hereinafter, the term "treatment" includes both pretreatment, before a pathological condition has arisen, and treatment after the condition has arisen. The term "treating" includes both treating the subject after the pathological condition has arisen, and preventing the development of the pathological condition.

While the invention has been described with respect to a limited number of embodiments, it will be appreciated that many variations, modifications and other applications of the invention may be made.

What is claimed is:

1. A composition for administering a cyclosporin compound, the composition comprising:
   (a) a dispersible concentrate characterized by being capable of forming, upon contact with an aqueous solution, particles of a size of less than about 100 nm, said dispersible concentrate comprising:
      (i) at least one surfactant; and
      (ii) an amphiphilic solvent comprising a lower alkyl hydroxy alkanoic acid ester or a lower alkyl ester of N-alkyl pyrrolidone; and
   (b) a pharmaceutically effective amount of the cyclosporin compound.

2. The composition of claim 1, wherein said lower alkyl hydroxy alkanoic acid ester includes ethyl lactate.

3. The composition of claim 1, wherein said amphiphilic solvent includes N-methyl pyrrolidone.

4. The composition of claim 1, wherein said amphiphilic solvent includes a combination of a lower alkyl ester of N-alkyl pyrrolidone an a lower alkyl hydroxy alkanoic acid ester.

5. The composition of claim 1, wherein said at least one surfactant is a combination of at least two surfactants, at least one surfactant of said combination being a hydrophilic surfactant and at least one surfactant of said combination being a hydrophobic surfactant.

6. The composition of claim 5, wherein said combination is a combination of polyoxyethylene(20)sorbitan monolaurate and sorbitan monooleate.

7. The composition of claim 5, further comprising:
   (c) an ethoxylated fat.

8. The composition of claim 7, wherein said ethoxylated fat is selected from the group consisting of polyethyleneglycol-hydrogenated castor oils.

9. The composition of claim 8, wherein said polyethyleneglycol-hydrogenated caster oil is selected from the group consisting of polyoxyl 35 castor oil, polyoxyl 40 hydrogenated castor oil, and polyoxyl 60 hydrogenated castor oil.

10. The composition of claim 7, further comprising:
    (d) a phospholipid.

11. The composition of claim 10, wherein said phospholipid is selected from the group consisting of egg phospholipid, bovine heart phospholipid, and soy phospholipid.

12. The composition of claim 10, further comprising:
    (e) a fatty acid ester.

13. The composition of claim 12, wherein said fatty acid ester is a solid fat at room temperature.

14. The composition of claim 13, wherein said fatty acid ester is tricaprin.

15. The composition of claim 1, wherein said particles size is less than about 60 nm.

16. The composition of claim 15, wherein said particle size is in a range of from about 5 nm to about 50 nm.

17. The composition of claim 1, wherein the cyclosporin compound is Ciclosporin.

18. A composition for administering a cyclosporin compound, the composition comprising a pharmaceutically effective amount of the composition of claim 1 and an aqueous solution as a diluent for said pharmaceutically effective amount of the composition of claim 1.

19. A composition for administering a cyclosporin compound, the composition comprising a lyophilized composition, said lyophilized composition being formed from a pharmaceutically effective amount of the composition of claim 1 and an aqueous solution as a diluent for said pharmaceutically effective amount of the composition of claim 1 to form a diluted solution, said diluted solution being lyophilized to form said lyophilized composition.

20. A method for administering a cyclosporin compound to a subject in need of treatment thereof, the method comprising the step of administering a pharmaceutically effective amount of the composition of claim 1 to the subject.

21. The method of claim 20, wherein said pharmaceutically effective amount of the composition of claim 1 is administered to the subject through oral administration.

22. The method of claim 21, wherein said pharmaceutically effective amount of the composition of claim 1 is administered as a dispersion with an aqueous solution as a diluent.

23. A method for determining storage stability of a formulation containing a cyclosporin compound, the method comprising the step of analyzing the composition of claim 1 for particle size, such that if said particle size is less than about 100 nm, the formulation is determined to be stable.

24. A composition for administering a cyclosporin compound, the composition comprising:
    (a) a dispersible concentrate characterized by being capable of forming, upon contact with an aqueous solution, particles of a size of less than about 100 nm, said dispersible concentrate comprising:
       (i) an ethoxylated fat; and
       (ii) an solvent comprising a lower alkyl hydroxy alkanoic acid ester or a lower alkyl ester of N-alkyl pyrrolidone; and
    (b) a pharmaceutically effective amount of the cyclosporin compound.

25. The composition of claim 24, wherein said ethoxylated fat is selected from the group consisting of polyethyleneglycol-hydrogenated castor oils.

26. The composition of claim 25, wherein said ethoxylated fat is selected from the group consisting of polyoxyl 35 castor oil, polyoxyl 40 hydrogenated castor oil, and polyoxyl 60 hydrogenated castor oil.

27. The composition of claim 24, wherein said amphiphilic solvent includes a lower alkyl hydroxy alkanoic acid ester.

28. The composition of claim 24, wherein said amphiphilic solvent includes ethyl lactate.

29. The composition of claim 24, wherein said amphiphilic solvent includes a lower alkyl ester of N-alkyl pyrrolidone.

30. The composition of claim 29, wherein said lower alkyl ester of N-alkyl pyrrolidone includes N-methyl pyrrolidone.

31. The composition of claim 24, wherein said amphiphilic solvent includes a combination of a lower alkyl ester of N-alkyl pyrrolidone and a lower alkyl hydroxy alkanoic acid ester.

32. The composition of claim 5, wherein said hydrophilic surfactant has an HLB (hydrophilic/lipophilic balance) of at least 8.

33. The composition of claim 5, wherein said hydrophobic surfactant has an HLB of less than 5.

34. The composition of claim 5, wherein said hydrophobic surfactant comprises a sorbitan fatty acid ester.

35. The composition of claim 5, wherein said hydrophobic surfactant comprises PEG-6 glyceryl monooleate.

36. The composition of claim 5, wherein said hydrophobic surfactant comprises propylene glycol laurate.

37. The composition of claim 5, wherein said hydrophilic surfactant comprises polyoxyethylene-sorbitan-fatty acid ester.

38. The composition of claim 5, wherein said hydrophilic surfactant comprises sucrose fatty acid ester.

39. The composition of claim 10, wherein said phospholipid comprises lecithin.

40. The composition of claim 1, further comprising amphiphilic solvent selected from the group consisting of ethylene glycol, glycofurol and PEG 400.

41. The method of claim 20, wherein said subject is in need of treatment of a condition selected from the group consisting of autoimmune disease and inflammatory conditions.

42. The method of claim 20, wherein said subject is in need of treatment of organ or tissue transplant rejection.

43. The method of claim 20, wherein said pharmaceutically effective amount of the composition of claim 1 is administered to the subject through administration.

44. The method of claim 20, wherein said pharmaceutically effective amount of the composition of claim 1 is administered to the subject through parenteral administration.

45. The method of claim 20, wherein said pharmaceutically effective amount of the composition of claim 1 is administered as a capsule.

46. The method of claim 20, wherein said pharmaceutically effective amount of the composition of claim 1 is administered as a tablet.

47. The method of claim 20, wherein said pharmaceutically effective amount of the composition of claim 1 is administered as a powder.

48. A method for administering a cyclosporin compound to a subject in need thereof, the method comprising the step of administering a pharmaceutically effective amount of a composition, said composition comprising a dispersible concentrate characterized by being capable of forming, upon contact with an aqueous solution, particles of a size of less than about 100 nm, said dispersible concentrate comprising at least one surfactant and an amphiphilic solvent comprising a lower alkyl hydroxy alkanoic acid ester or a lower alkyl ester of N-alkyl pyrrolidone.

49. A composition for administering a cyclosporin compound, the composition comprising:

(a) a dispersible concentrate characterized by being capable of forming, upon contact with an aqueous solution, a solid particulate suspension containing the cyclosporin compound, said particulate suspension containing particles of a size of less than about 100 nm, said dispersible concentrate comprising:

(i) at least one surfactant; and (ii) an amphiphilic solvent comprising a lower alkyl hydroxy alkanoic acid ester or a lower alkyl ester of N-alkyl pyrrolidone; and (b) a pharmaceutically effective amount of the cyclosporin compound.

* * * * *